United States Patent [19]
Melin et al.

[11] Patent Number: 6,143,722
[45] Date of Patent: Nov. 7, 2000

[54] HEPTAPEPTIDE OXYTOCIN ANALOGUES

[75] Inventors: Per Melin, Malmö; Anders Nilsson, Lund, both of Sweden; Jerzy Trojnar, Solana Beach, Calif.; Carl-Johan Aurell, Mölndal, Sweden; Pierre Riviere, San Diego, Calif.; Robert Haigh, Hants, United Kingdom

[73] Assignee: Ferring, B.V., Hoofddorp, Netherlands

[21] Appl. No.: 09/308,912

[22] PCT Filed: Nov. 21, 1997

[86] PCT No.: PCT/SE97/01968

§ 371 Date: Aug. 2, 1999

§ 102(e) Date: Aug. 2, 1999

[87] PCT Pub. No.: WO98/23636

PCT Pub. Date: Jun. 4, 1998

[30] Foreign Application Priority Data

Nov. 26, 1996 [SE] Sweden .................................. 9604341

[51] Int. Cl.⁷ .............................. A61K 38/00; C07K 5/00; C07K 7/00

[52] U.S. Cl. ............................ 514/17; 530/315; 530/329; 530/330

[58] Field of Search ................................ 514/17; 530/315, 530/329, 330

[56] References Cited

FOREIGN PATENT DOCUMENTS 9200996  1/1992  WIPO .
9502609  1/1995  WIPO .

*Primary Examiner*—Avis M. Davenport
*Attorney, Agent, or Firm*—Hopgood, Calimafde Kalil & Judlowe

[57] ABSTRACT

Heptapeptide analogues or pharmaceutically acceptable salts thereof consist of a hexapeptide moiety S and a C-terminal β-aminoalcohol residue Z bound to the moiety S by an amide bond, wherein the β-aminoalcohol Z is —NR—CH(Q)—CH$_2$OH, Q is (CH$_2$)$_n$—NH—A is H or —C(=NH)NH$_2$, and R is CH$_3$ or C$_2$H$_5$, and the moiety S wherein H is a D-aromatic α-aminoacid and Y is an aliphatic α-aminoacid and have oxytocin antagonist activity. Also disclosed is: a method of their synthesis; pharmaceutical compositions containing these analogues; the synthesis of such compositions; a method of control of uterine contractions.

28 Claims, No Drawings

HEPTAPEPTIDE OXYTOCIN ANALOGUES

This application is a 371 of PCT/SE97/01968 filed Nov. 21, 1997.

FIELD OF THE INVENTION

The present invention relates to new heptapeptide analogues (i.e. heptapeptides in which the N-terminal residue is deaminated and the C-terminus is reduced to an alcohol) exhibiting oxytocin antagonist activity useful, inter alia, for decreasing or blocking uterus muscle contraction associated with pre-term labour and menstrual pain. The invention also relates to pharmaceutical compositions containing these peptide analogues and to their use.

BACKGROUND OF THE INVENTION

Oxytocin is a peptide hormone. It stimulates contraction of the uterine muscles. For this reason, it is believed to be involved in the etiology of pre-term labour and menstrual pain. It is further believed that oxytocin antagonists would be useful in the control of these conditions. Oxytocin antagonist peptides of adequate potency and selectivity of therapeutic use are known. They are often intended for administration in aqueous solution. The manufacture of ready-for-use doses of such antagonists requires that the solutions be stable for extended periods, which is not always true. In such cases, the medicament must be prepared immediately prior to use from, for instance, the freeze-dried peptide or its pharmaceutically acceptable salt. This sort of manipulation is inconvenient and entails the risk of contamination.

OBJECTS OF THE INVENTION

It is an object of the invention to provide new oxytocin antagonists which are heptapeptide analogues having improved stability in aqueous media while retaining adequate potency and selectivity for therapeutic efficacy.

It is a second object of the invention to provide pharmaceutical compositions containing said new heptapeptide-analogue oxytocin antagonists and having improved stability and, therefore, shelf-life.

It is a further object of the invention to provide for a method of treatment of a medical condition associated with excess or inappropriate uterine contraction, which method is the administration of a pharmaceutical composition containing said heptapeptide analogue.

SUMMARY OF THE INVENTION

The invention comprises a class of compounds which are heptapeptide analogues, pharmaceutical compositions containing such analogues, and a use for these compositions which is the treatment of uterine contractions, particularly in the context of pre-term labour and menstrual pain.

The heptapeptide analogues of the invention have an N-terminal hexapeptide moiety S and a C-terminal β-aminoalcohol Z, which is considered hereinafter to be the formal equivalent of the seventh amino acid of the heptapeptide. The moiety S has the structure:

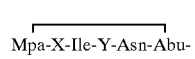

wherein Mpa, Ile, Asn and Abu have the following meanings:

| | |
|---|---|
| Mpa | 3-mercaptopropionic acid residue (otherwise called desamino-cysteine) |
| Ile | isoleucine residue |
| Asn | asparagine residue |
| Abu | α-aminobutyric acid residue; | and wherein X is an aromatic D-α-amino acid and Y is an aliphatic α-amino acid.

The aminoalcohol Z has the structure:

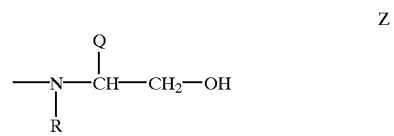

wherein

R is methyl or ethyl, and

Q is —(CH$_2$)$_n$—NH—A, where n is 1–6 and A is H or —C(=NH)NH$_2$.

The compounds of the invention can form acid addition salts, and to the extent that these salts are pharmaceutically acceptable they are included within the scope of the invention.

The compounds can be incorporated into either solid or liquid formulations. Examples of such formulations include tablets, capsules, solutions and suspensions. Other components of such formulations can include, for example, diluents, dispersants, preservatives, buffering agents, flavouring agents and osmotic pressure regulating agents. Solid formulations are particularly suitable for oral administration, while solutions are most useful for injection (i.v., i.m. or s.c.) or intranasal administration. A particular merit of the compounds of the invention is that their solutions are more stable on prolonged storage than those of previously known compounds of comparable potency.

The formulated pharmaceutical is useful in the control of uterine contractions. Two indications where such control is likely to be required are pre-term labour and menstrual pain. When used in the management of pre-term labour, the pharmaceuticals can be used as acute tocolytic agents following the onset of labour and as maintenance therapy for preventing the recurrence of such episodes.

DETAILED DESCRIPTION OF THE INVENTION

According to the present invention are disclosed heptapeptide analogues exhibiting therapeutically useful oxytocin antagonist activity and having improved stability in aqueous media.

The heptapeptide analogues of the invention are characterised by a structure which comprises an N-terminal hexapeptide analogue moiety S and a C-terminal β-aminoalcohol moiety Z. The structure of the β-aminoalcohol Z is:

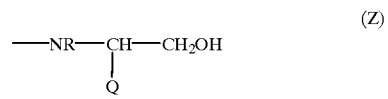

wherein Q is —(CH$_2$)$_n$—NH—A, n is 1–6 and A is H or —C(=NH)NH$_2$, and wherein R is CH$_3$ or CH$_2$H$_5$;

and the moiety S is $$\text{Mpa-X-Ile-Y-Asn-Abu-} \tag{S}$$

wherein Mpa, Ile, Asn and Abu have the following meanings:

| | |
|---|---|
| Mpa | 3-mercaptopropionic acid residue (otherwise called desamino-cysteine) |
| Ile | isoleucine residue |
| Asn | asparagine residue |
| Abu | α-aminobutyric acid residue; | and wherein

X is a D-aromatic α-amino acid; and
Y is an aliphatic α-amino acid.

By an aromatic α-amino acid is meant an α-amino acid wherein the side chain includes an aromatic ring system. Such a system may be carbocyclic or heterocyclic, monocyclic or fused. Examples of aromatic α-amino acids include (but are not limited to) phenylalanine, tyrosine, (O-ethyl) tyrosine, tryptophan, β-(2-naphthyl)alamine and phenylglycine. It will be noted that the residue X is of the unnatural D-configuration in the compounds of the invention.

By an aliphatic α-amino acid is meant an α-amino acid wherein the side chain has only carbon and hydrogen atoms. Such side chains will include alkyl and cycloalkyl groups. They may be unsaturated, but may not include aromatic residues. Side chains of 1 to 12 carbon atoms are included, although the preferred range is for 3–7 carbon atoms. Examples of aliphatic α-amino acids include (but are not limited to) alanine, valine, leucine, cyclohexylglycine and adamantylalanine. The residue Y has the natural L-configuration.

In the structure of the hexapeptide analogue moiety S, the line joining the Mpa and Abu residues has its conventional meaning. It signifies that there is a covalent bond linking the ends of the side chains of these two residues. In this case, the sulphur atom of the Mpa residue is joined by a covalent bond to the γ- (or 4-) carbon atom of the Abu residue.

The aminoalcohol moiety Z includes a stereogenic centre and so can exist in two epimeric forms, R and S, corresponding to the D and L isomers of the related amino acids. Heptapeptide analogues with either of these isomers are included within the scope of the invention, as are mixtures of epimers. Preferably, the aminoalcohol moiety is present as a single epimer, and preferably it has the S configuration.

In the context of the present invention, the Mpa residue and the aminoalcohol Z are considered to be formal equivalents of α-amino acids, and the compounds of the invention are termed heptapeptide analogues accordingly.

In a preferred embodiment of the invention, X is either a D-tryptophan residue or a β-(2-naphthyl)-D-alanine residue.

In another preferred embodiment of the invention, Y is a residue of one of valine, leucine, isoleucine, alloisoleucine, cyclohexylalanine and (β,β-diethyl)alanine.

In another preferred embodiment of the invention, n is in the range 2–4.

In a more preferred embodiment of the invention, X is either a D-tryptophan residue or a β-(2-naththyl)-D-alanine residue and Y is a residue of one of valine, leucine, isoleucine, alloisoleucine, cyclohexylalanine and (β,β-diethyl)alanine.

A particularly preferred embodiment of the invention is a peptide analogue chosen from:

Mpa-D-Trp-Ile-alloIle-Asn-Abu-N—CH—CH$_2$OH
|  |
CH$_3$  CH$_2$CH$_2$CH$_2$NH$_2$ Mpa-D-Trp-Ile-alloIle-Asn-Abu-N—CH—CH$_2$OH
|  |
CH$_3$  CH$_2$CH$_2$CH$_2$CH$_2$NH$_2$ Mpa-D-Trp-Ile-alloIle-Asn-Abu-N—CH—CH$_2$OH
|  |
CH$_3$  CH$_2$CH$_2$NH$_2$ Mpa-D-Trp-Ile-alloIle-Asn-Abu-N—CH—CH$_2$OH
|  |
CH$_3$  CH$_2$CH$_2$CH$_2$NH$_2$—C=NH
|
NH$_2$ Mpa-D-Trp-Ile-Ala(3,3-diethyl)-Asn-Abu-N—CH—CH$_2$OH
|  |
CH$_3$  CH$_2$CH$_2$CH$_2$NH$_2$ Mpa-D-Nal-Ile-alloIle-Asn-Abu-N—CH—CH$_2$OH
|  |
CH$_3$  CH$_2$CH$_2$CH$_2$NH$_2$ Mpa-D-Nal-Ile-Ala(3,3-diethyl)-Asn-Abu-N—CH—CH$_2$OH
|  |
CH$_3$  CH$_2$CH$_2$CH$_2$NH$_2$ Mpa-D-Trp-Ile-Ile-Asn-Abu-N—CH—CH$_2$OH
|  |
CH$_3$  CH$_2$CH$_2$CH$_2$NH$_2$ Mpa-D-Trp-Ile-Leu-Asn-Abu-N—CH—CH$_2$OH
|  |
CH$_3$  CH$_2$CH$_2$CH$_2$NH$_2$ Mpa-D-Trp-Ile-Val-Asn-Abu-N—CH—CH$_2$OH
|  |
CH$_3$  CH$_2$CH$_2$CH$_2$NH$_2$ Mpa-D-Trp-Ile-Cha-Asn-Abu-N—CH—CH$_2$OH
|  |
CH$_3$  CH$_2$CH$_2$CH$_2$NH$_2$ wherein the following further abbreviations have been used:

| | |
|---|---|
| D-Trp | D-tryptophan residue |
| alloIle | alloisoleucine residue |
| Ala(3,3-diethyl) | (β,β-diethyl)alanine residue |
| D-Nal | β-(2-naphthyl)-D-alanine residue |
| Leu | leucine residue |
| Val | valine residue |
| Cha | β-cyclohexylalanine residue. |

A most preferred embodiment of the invention is the peptide analogue:

Mpa-D-Trp-Ile-alloIle-Asn-Abu-N—CH—CH$_2$OH
|  |
CH$_3$  CH$_2$CH$_2$CH$_2$NH$_2$.

The compounds of the invention contain a basic site (amine or guanidine) and so can form salts with acids, which salts retain the pharmacological properties of the free bases. Accordingly, such salts are included within the scope of the invention. Examples of such salts include (but are not limited to) the hydrochloride, hydrobromide, sulphate, acetate, citrate, benzoate, trifluoroacetate and methanesulphonate.

Also disclosed according to the invention are pharmaceutical compositions which include a pharmacologically effective amount of at least one of the oxytocin antagonist heptapeptide analogues described above. The composition may also include pharmaceutically acceptable additives such as preservatives, diluents, dispersing agents, agents to promote mucosal absorption (examples of which are disclosed by Merkus, F. W. H. M. et al., J. Controlled Release 24, 201–208, 1993, and which include surfactants, bile acids, fusidates, phospholipids and cyclodextrins), buffering agents and flavourings. Such compositions may be formulated as solids (for example as tablets, capsules or powders) or liquids (for example as solutions or suspensions), which is here taken to include creams and ointments, for oral or parenteral administration. Oral (including sublingual and buccal), intranasal, pulmonary, transdermal, rectal, vaginal, subcutaneous, intramuscular and intravenous administration may all be suitable routes for dosing.

A preferred composition according to the invention is a sterile aqueous solution of a heptapeptide analogue as described, and particularly an isotonic saline solution suited to intranasal administration or intravenous injection. The solution may contain a buffering agent to maintain the pH of the solution in the range 0.3–7.0, and preferably in the range 3.5–5.5. The buffer is, for example, a phosphate/citrate buffer.

Another preferred composition according to the invention is a tablet for oral administration. Particularly preferred is a tablet which is coated with a substance that is substantially insoluble at low pH such as is present in the stomach, but which dissolves at the more neutral pH of the small intestine to release the peptide analogue for absorption. Examples of such coatings are disclosed in PCT/SE94/00244 and in PCT/SE95/00249, which are incorporated into this specification by reference.

A further disclosure of the invention is a method of reducing or stopping unwanted contractions of the uterine muscles. This method is the administration to the subject of an effective amount of one of the oxytocin antagonist heptapeptide analogues of the invention, preferably formulated as a composition as described above. It will be evident that this disclosure of the invention is equally the disclosure of a use for the compounds and formulations of the invention.

A particularly preferred embodiment of the invention is a method of stopping the contractions of the uterus in pre-term labour. Following the initial intervention, which will involve a period of 1–3 days, the treatment may be continued to a prevent a recurrence of labour until such time as the attending physician sees fit. Thus there are two aspects to this embodiment, an acute tocolytic use and a maintenance therapeutic use.

Another preferred embodiment of the invention is a method of reducing painful contractions of the uterus associated with menstruation.

The amount of heptapeptide analogue which constitutes a therapeutically effective dose will depend on a number of factors. The route of administration will be an important consideration. Intravenous injection is likely to be the most efficient route of delivery, while intranasal administration can be expected to be efficient than oral dosing. Accordingly, less compound will be required for a single intravenous dose than for a single intranasal dose, and more compound will be required for a single oral dose. The attending physician will also need to take into account factors such as the age, weight and state of health of the patient. The management of menstrual pain is also likely to require less compound than is pre-term labour. The amount of compound which constitutes a single effective dose for intravenous treatment of an average woman in pre-term labour is from about 0.1 mg to about 500 mg, and preferably from about 1 mg to about 200 mg, in a period of 24 hours.

The heptapeptide analogues of the present invention selectively inhibit uterine muscle contractions while lacking undesirable oxytocin agonist properties. They also have little or no antidiuretic, hypotensive or hypertensive effect, which might potentially be side effects of analogues of oxytocin and the related hormone vasopressin. They are comparable in potency to those compounds known in the art which they most resemble structurally. They differ from these compounds, which are disclosed in WO95/02609, in the nature of the C-terminal residue. The known compounds have a carboxamide function (—$CONH_2$) where the compounds of the present invention have a primary alcohol (—$CH_2OH$). The compounds of the present invention are superior to those of WO95/02609 in respect of their stability, particularly in aqueous media. This is clearly an advantage when the compound is to be formulated as an aqueous solution which will consequently have a longer shelf-life and have less stringent requirements for refrigeration, but it is also an advantage in the manufacturing and formulating processes, which will involve periods when the compound is in solution even if the final composition is a solid.

While it has been emphasised above that the compounds of the invention are particularly useful in the control of uterine muscle contractions, it will be appreciated by one familiar with the art that other therapeutic uses for oxytocin antagonists are possible. For example, another target of oxytocin action is the mammary gland, where it promotes milk ejection. The compounds of the invention might therefore be used to control inappropriate lactation. They might also be useful in the control of certain tumours, particularly mammary tumours and secondary metastases derived from a primary mammary tumour. Hyperplasia of the prostate might be a further therapeutic target. It has also been suggested that oxytocin is involved in luteal development and the facilitation of post-coital sperm transport. From this it can be inferred that the compounds of the invention might be useful as contraceptive or fertility-regulating agents. Another peripheral target of oxytocin is the immune system. Oxytocin antagonists are therefore potentially useful as immunomodulating and anti-inflammatory agents. Oxytocin is also present in the brain, where it has been suggested to have a role in the etiology of such diverse conditions as psychogenic erectile dysfunction, schizophrenia and alcohol-induced neuropsychological deficiencies. In some species it has been shown to have an effect on complex social behaviour. Accordingly, the compounds of the invention might be used as, for example, anti-psychotic or cognition-enhancing agents. The use of the compounds of the invention in any of these therapeutic situations is intended to fall within the scope of this disclosure.

In the following, the invention will be described in general and by means of specific examples. It should be understood that this description is not intended to limit the scope of the invention, and that such variations as are known in the art and which the practitioner would consider to be equivalent fall equally within that scope.

GENERAL METHODS FOR SYNTHESIS

The chemical transformations necessary to effect the synthesis of the compounds of the invention are well known in the art. The techniques of peptide chemistry both in solution and an solid supports are particularly relevant. Solution phase methods are described in the following references:

Law, H. B. and Du Vigneaud, V., J. Am. Chem. Soc. 82, 4579–4581, 1960;

ZhuZe, A. L. et al., Coll. Czech. Chem. Comm. 29, 2648–2662, 1964; and

Larsson, L.-E. et al., J. Med. Chem. 21, 352–356, 1978.

Solid phase methods are discussed in:

Merrifield, R. B., J. Am. Chem. Soc. 85, 2149, 1963;

Merrifield, R. B., Biochemistry 3, 1385, 1964; and

König, W. and Geiger, R., Chem. Ber. 103, 788, 1970.

The route used by the inventors is discussed in outline below and then exemplified in detail. It will be apparent to one familiar with the practice of peptide chemistry that the order in which some of the transformations are performed can be varied. It is not the intention of the inventors that such obvious variations should be excluded from the scope of the invention.

Most frequently, the starting material will be a protected N-alkyl amino acid of general formula 1.

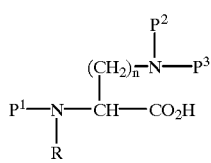

R and n are chosen from the possibilities outlined previously. $P^1$ is a nitrogen protecting group. One particularly favoured choice of $P^1$ is 9-fluorenylmethyloxycarbonyl (Fmoc).

When A in the target compound is to be H then either $P^2$ is a nitrogen protecting group distinguishable from $P^1$ (for example benzyloxycarbonyl) and $P^3$ is H or the same as $P^2$, or $P^2$ and $P^3$ together are a divalent protecting group for nitrogen (for example phthaloyl).

When A is to be —C(=NH)NH$_2$ then $P^2$ is either H or a protecting group as above and $P^3$ is —C(=NP$^4$)NH$_2$, where $P^4$ is a protecting group, and is preferably the same as $P^2$. It will be apparent to the practitioner that these protected guanidines can exist as tautomers and positional isomers. Although —(CH$_2$)$_n$—N(P$^2$)P$^3$ has been defined as $2^A$, isomers $2^B$, $2^C$ and $2^D$ can all be considered as equivalent to this structure for the purposes of this description.

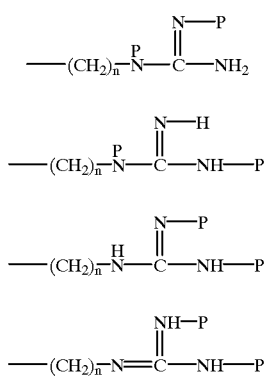

When the protected N-alkyl amino acids of general formula 1 are not commercially available they can be prepared by methods described in the literature, or by methods analogous to them.

Assuming that solid phase methods are to be used, the amino acid 1 is attached to a suitable resin to give 3 as a first intermediate.

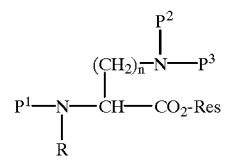

where Res represents the polymeric resin.

$P^1$ is a cleaved and FmocAbu(SCH$_2$CH$_2$CO$_2$t-Bu)OH is coupled to give 4.

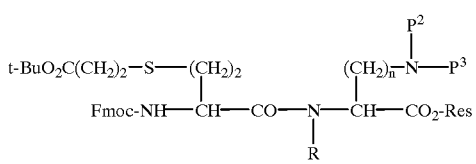

The peptide is extended by sequential coupling with FmocAsn, FmocY, FmocIle and then BocX. When X is D-Trp it is advantageous to protect the indole nitrogen as its formyl derivative. The use of Boc-protection for this amino acid allows for simultaneous cleavage of the t-butyl ester and the N-terminal protecting group. At this stage, intermediate 5 is present.

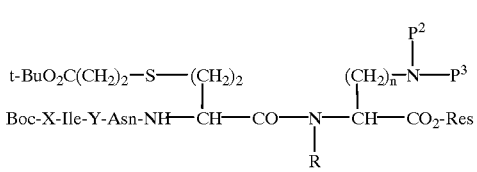

The peptide is cleaved from the resin using appropriate standard conditions and then esterified, for example by treatment with benzyl bromide to give the benzyl ester 6.

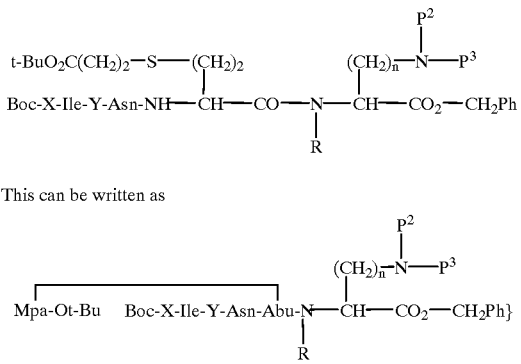

The Boc group and the t-butyl ester are cleaved by acid treatment, and the resulting amine and acid groups are condensed to form the macrocycle. The benzyl ester is then reduced to give the primary alcohol of the target compound, for example by reaction with sodium borohydride in aqueous isopropanol. Conveniently, the removal of the remaining protecting groups can also be achieved during this conversion. If that is not the case, a final deprotection step is necessary. The product is isolated and purified using standard techniques.

The following specific examples were prepared according to this general outline. They are representative of the compounds of the present invention. The following abbreviations are used:

| TBTU | 2-(1-H-benzotriazol-1-yl)-1,1,3,3-tetramethyluronium tetrafluoroborate |
|------|---|
| Boc | tert-butyloxycarbonyl |
| Fmoc | 9-fluorenylmethyloxycarbonyl |
| TFA | trifluoroacetic acid |
| DMF | dimethylformamide |
| DBU | 1,8-diazabicyclo[5.4.0]undec-7-ene |
| Bn | benzyl |
| Orn | ornithine |
| Pht | phthaloyl |

Protected amino acids were obtained as follows:

FmocAbu(SCH$_2$CH$_2$CO$_2$t-Bu) prepared according to Prochazka, E. et al., Coll. Czech. Chem. Comm. 57, 1335, 1992;

FmocN$^\alpha$MeOrn(Pht) prepared by analogy to the route used for the Lysine derivative by Freidinger, R. M. et al., J. Org. Chem. 48, 77, 1983;

Fmoc-alloIle prepared according to Ten Kortenaar, P. B. W. et al., Int. J. Peptide Protein Res. 27, 398, 1986;

FmocAla(3,3-diethyl) prepared according to Eisler, K. et al., Coll. Czech. Chem. Comm. 31, 4563, 1966;

Boc-D-Trp(CHO); Boc-D-Nal; FmocAsn; FmocIle; FmocVal; FmocLeu; FmocCha all from Bachem (CH and USA).

EXAMPLE I

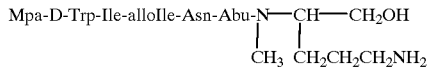

Ia:

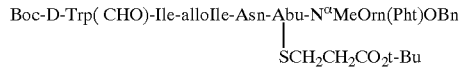

Peptide Ia was synthesised using solid phase methodology on o-chlorotrityl resin and with the Fmoc strategy.

The first amino acid, FmocN$^\alpha$MeOrn(Pht)OH, was attached to the resin. Cleavage of the Fmoc group was achieved with 2% DBU in DMF. Other residues were coupled sequentially, finishing with Boc-D-Trp(CHO)OH. The resin-bound peptide was treated with a mixture of acetic acid/trifluoroethanol/dichloromethane (1:2:7), then the mixture was filtered and the filtrate was evaporated and freeze dried. The resulting peptide acid was esterified by reaction with benzyl bromide (2 eq.) and diisopropylethylamine (2.5 eq) in DMF for 27 h. The solvent was evaporated and the residue was freeze dried from acetic acid.

Ib:

The N-terminal Boc group and the t-butyl ester of Ia were cleaved by treatment with 95% TFA/2.5% anisole/2.5% water for 1.5 h at room temperature. TFA was evaporated and the produce was precipitated by the addition of diethyl ether. The peptide was cyclised by treatment with TBTU (1 eq) and N-methylmorpholine (17 eq) in DMF at room temperature. The solvent was evaporated and the peptide Ib was purified by reversed phase chromatography.

Ic:

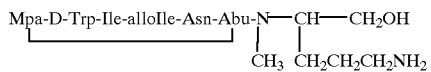

The purified benzyl ester Ib was treated with NaBH$_4$ (7 eq) in solution in a mixture of isopropanol/water (6:1) at room temperature for 22 h under an inert gas atmosphere. Acetic acid (18 eq) was added and the mixture was heated at 80° C. for 6 h. The solvent was evaporated and the product peptide Ic (≡"peptide I") was purified by reversed phase liquid chromatography: stationary phase: mobile phase; acetonitrile/0.1% TFA in water. Yield 14 mg. Mass spectrometry (electrospray ionisation, ion trap analysis, positive mode) indicated a molecular mass in agreement with the proposed structure (found m/z=830.5 [MH$^+$]; calc. for [C$_{40}$H$_{63}$N$_9$O$_8$S$^1$H$^+$] m/z=830.5).

EXAMPLES II–VII

Using the same method as for Example I, and by substituting the appropriate protected amino acids for Boc-D-Trp)CHO)OH and Fmoc-alloIleOH, the peptides listed in Table 1 were prepared.

TABLE 1

Mass spectroscopy data

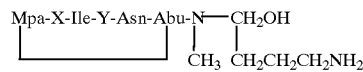

| | | | Mass spec. | |
|---|---|---|---|---|
| Peptide | X | Y | Calc. MH$^+$ | Found |
| II | D-Trp | Leu | 830.5 | 830.4 |
| III | D-Trp | Val | 816.4 | 816.4 |
| IV | D-Trp | Cha | 870.5 | 870.5 |
| V | D-Trp | Ile | 830.5 | 830.5 |
| VI | D-Nal | alloIle | 841.5 | 841.5 |
| VII | D-Trp | Ala(3,3-diethyl) | 844.5 | 844.5 |

A number of reference peptide amides were prepared according to the methods disclosed in WO95/02609 in order to compare the properties of the present invention with those known in the art. These reference peptides are listed in Table 2.

TABLE 2

Reference peptides

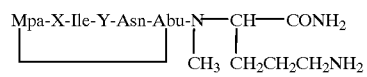

| Peptide | X | Y |
|---|---|---|
| r-IX | D-Trp | alloIle |
| r-X | D-Trp | Val |
| r-XI | D-Nal | alloIle |

EXAMPLE VIII

Using the method of Example I, but substituting N$^\alpha$-ethylornithine for the N$^\alpha$-methyl amino acid, the following peptide (VIII) was prepared (found m/z=855.1 [MH$^+$]; calc. for [C$_{41}$H$_{65}$N$_9$O$_8$S+H$^+$] m/x=855.5).

Peptide VIII

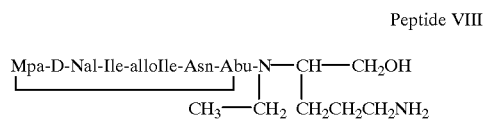

EXAMPLE IX

Biological Evaluation of Compounds

The compounds of the present invention can be assessed in a number of in vitro and in vivo biological systems. These test systems are chosen to be as relevant to the intended human patient as possible.

i) Oxytocin receptor binding assay

Recombinant human oxytocin receptors were expressed in either CHO or HEK293 cells using standard molecular biological techniques. A membrane fraction was prepared and incubated in the presence of [$^{125}$I]-oxytocin and varying concentrations of heptapeptide analogue. Membranes were then isolated by filtration and counted for radioactivity to determine oxytocin binding. An inhibition constant K$_i$ was determined for the analogue. The results obtained are presented in Table 3.

TABLE 3

Oxytocin receptor assay; inhibition constants K$_i$

| Peptide | K$_i$ (nM); mean ± SEM |
|---------|------------------------|
| I       | 0.25 ± 0.16            |
| II      | 3.2 ± 0.75             |
| III     | 0.80 ± 0.30            |
| IV      | 7.0 ± 1.85             |
| V       | 1.4 ± 0.15             |
| VI      | 0.1 ± 0.0              |
| VII     | 2.4 ± 0.85             | ii) Antagonist effect in vitro in a human uterus model

Uterus muscle tissue from women in late pregnancy undergoing Caesarean section was cut into strips which were mounted in a tissue bath filled with Krebs-Ringer buffer and oxygenated with carbogen (95% O$_2$+5% CO$_2$) gas. Changes in isometric muscle tension detected with a tension transducer were recorded on a Grass polygraph.

The concentration-effect curve of oxytocin was recorded. The effect measured in this case corresponds to the net value of the integrated contraction curve during the 10 minute period following agonist (i.e. oxytocin) administration. A concentration of oxytocin giving at least half-maximal response was selected. This concentration of agonist was administered to the tissue in the presence of different concentrations of antagonist heptapeptide analogue and the response was recorded. The concentration of antagonist required to reduce the response to 50% of its control value was determined by regression analysis and is given here as an IC$_{50}$ value. [IC$_{50}$ value=concentration of antagonist required to reduce the effect of a given agonist dose by 50%]. The results are given in Table 4.

TABLE 4

Inhibition of agonist effect (uterus model)

| Peptide | IC$_{50}$, human uterus model (nM) |
|---------|------------------------------------|
| I       | 5 ± 1                              |
| r-VIII  | 18 ± 3                             | iii) In vivo rat model

Sprague Dawley rats (ca. 250 g) in natural estrus were anaesthetised with Inactin (0.5 mg/100 g body weight, i.p.). The activity of the myometrium was measured with the aid of a catheter fixed in the uterine cavity and filled with modified Lockes solution. The catheter was connected to a Statham P23D force transducer and the contractions were recorded on a Grass polygraph (model 7D).

The dose-response curve for oxytocin (2×10$^{-4}$–5×10$^{-3}$ μmol/kg) was recorded. In this case the response was quantified by integration of the curve during the 15 minutes following agonist injection. A dose of oxytocin giving an effect corresponding to an intralumenar contraction pressure of 10–30 mm Hg and within the linear section of the curve was selected. This dose of oxytocin was administered to the animal in conjunction with at least two different doses of antagonist and the effect was recorded. The dose of antagonist which reduces the effect of the agonist to 50% of tis control value was determined by interpolation and is given here as an ID$_{50}$ value. [ID$_{50}$ value=dose of antagonist required to reduce the effect of a given agonist dose by 50%]. The results are given in Table 5.

The duration of action of the antagonists was also determined in this model. An oxytocin dose was selected (2×10$^{-4}$–5×10$^{-3}$ μmol/kg) giving an effect corresponding to half the maximum effect (this dose is the ED$_{50}$). The effect determined here is the same as for the ID$_{50}$ determination defined above. An antagonist dose was selected (8×10$^{-4}$–4×10$^{-3}$ μmol/kg) so as to give at least 50% inhibition of the response to the agonist. At the beginning of the experiment, single doses of the agonist and antagonist were co-administered. At 20 minute intervals thereafter, doses of the agonist alone were administered and the response was measured. The time taken for the inhibition of the agonist effect to decline to 25% of its starting value was determined by interpolation and is given here as the t$_{75}$ value. [t$_{75}$ value=time period required for the effectiveness of a single dose to decline by 75%]. The results are presented in Table 5.

TABLE 5

Inhibition of agonist effect (in-vivo rat model)

| Peptide | ID$_{50}$, rat model (nmol/kg) | t$_{75}$, rat model (min) |
|---------|-------------------------------|--------------------------|
| I       | 2.9 ± 0.3                     | 169 ± 2                  |
| r-IX    | 2.9 ± 0.3                     | 180 ± 9                  |

It is evident from the results presented in Tables 3–5 that the compounds of the present invention are at least as good as the earlier compounds in the rat model, both in terms of potency and duration of action, and that they are superior to the earlier compounds in the more relevant human model.

EXAMPLE X

Pharmaceutical Formulations

Solution in isotonic buffered saline for i.v. injection.

The following solutions were prepared:

| Solution A (0.02M citric acid) | |
|---|---|
| citric acid monohydrate | 0.42 g |
| distilled water | ad 100 ml |
| Solution B (0.04M disodium hydrogen phosphate) | |
| Na$_2$HPO$_4$.2H$_2$O | 0.712 g |
| distilled water | ad 100 ml |

To 27 ml of solution A is added 23 ml of solution B, 0.81 g of NaCl and 0.322 g of peptide I acetate. The pH is adjusted to 4.5 with solution A, then distilled water is added to give a total volume of 100 ml. Finally, the mixture is filtered through Sterivex-GV 0.22 μm. This gives an isotonic solution containing 0.3 mg/ml of peptide I (calculated as free base) suitable for intravenous injection.

Tablets for oral administration

The following components were combined:

| Peptide I acetate | 108 mg |
|---|---|
| mannitol | 7.7 g |
| lactose | 6.0 g |
| microcrystalline cellulose | 6.0 g |
| crosslinked carboxymethyl cellulose | 200 mg |
| talcum | 800 mg |
| magnesium stearate | 200 mg |
| polyvinylpyrrolidone/ethanol | to bind |

The blended mixture was formed into tablets using standard methods. The mixture is sufficient to prepare 100 tablets containing 1 mg of peptide I (calculated as free base) each.

Enteric tablet for oral administration 25 of the aforementioned tablets were air-spray coated with 100 mg of cellulose acetate phthalate (4 mg per tablet).

Also useful in the invention is the composition disclosed in WO 95/25534 in which the active agent (desmopressin, for instance), can be substituted by the compounds according to the present invention. The adaptation of the composition to handle the higher amounts of active agents required to be incorporated into the tablet is within the easy reach of the person skilled in the art.

EXAMPLE XI

Evaluation of Stability

Solutions of the heptapeptide analogues of the present invention were prepared with compositions representative of aqueous formulations. The solutions were stored for several weeks at 50° C. and aliquots were withdrawn periodically for analysis by HPLC. Reference peptides were studied in parallel. Degradation was determined as the loss of peptide (% by weight per week), independent of the nature of the decomposition products. The results are presented in Table 6.

TABLE 6

Stability test

| Peptide | Composition of test solution | Degradation at 50° C. (wt %/week) |
|---|---|---|
| I | Isotonic citrate/phosphate buffer, pH 4.5 | 0.4 |
| r-IX | as above | 2.9 |
| III | as above | 0.7 |
| r-X | as above | 4.3 |
| VI | as above | 1.2 |
| r-XI | as above | 4.0 |

The results presented above clearly indicate that the compounds of the invention are more stable in solution than the previously described compounds. In practice, this increased stability means that aqueous formulations will have a longer shelf-life and be less demanding in their need for refrigerated storage. Besides the financial savings which result, there will be benefits in both convenience and safety because the need to prepare individual doses immediately prior to administration will be reduced.

The manufacturing process will also benefit, since the compounds will be more resistant to decomposition during and after purification.

What is claimed is:

1. A heptapeptide analogue, or a pharmaceutically acceptable salt thereof, having oxytocin antagonist activity and consisting of a hexapeptide moiety S and a C-terminal β-aminoalcohol residue Z bound to the moiety S by an amide bond, wherein the β-aminoalcohol Z is:

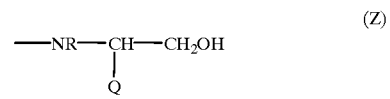

wherein Q is (CH$_2$)$_n$—NH—A, n is 1–6 and A is H or —C(=NH)NH$_2$, and wherein R is CH$_3$ or C$_2$H$_5$;
and the moiety S is:

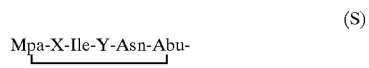

wherein Mpa, Ile, Asn and Abu have the following meaning:

| Mpa | 3-mercaptopropionic acid residue |
|---|---|
| Ile | isoleucine residue |
| Asn | asparagine residue |
| Abu | α-aminobutyric acid residue | and wherein
X is a D-aromatic α-amino acid; and
Y is an aliphatic α-amino acid.

2. The heptapeptide analogue of claim 1, wherein X is the amino acyl residue of D-tryptophan or β-(2-naphthyl)-D-alanine.

3. The heptapeptide analogue of claim 2, wherein Y is the amino acyl residue of leucine, valine, isoleucine, alloisoleucine, β,β-diethylalanine, cyclohexylalanine or cyclohexylglycine.

4. The heptapeptide analogue of claim 1, wherein Y is the amino acyl residue of leucine, valine, isoleucine, alloisoleucine, β,β-diethylalanine, cyclohexylalanine or cyclohexylglycine.

5. The heptapeptide analogue of claim 4 in which n is 2, 3 or 4.

6. The heptapeptide analogue of claim 1 in which n is 2, 3 or 4.

7. The heptapeptide analogue of claim 6, wherein X is the amino acyl residue of D-tryptophan or β-(2-naphthyl)-D-alanine.

8. The heptapeptide analogue of claim 1, wherein X is the amino acyl residue of D-tryptophan or β-(2-naphthyl)-D-alanine, Y is the amino acyl residue of leucine, valine, isoleucine, alloisoleucine, β,β-diethylalanine, cyclohexylalanine or cyclohexylglycine, and n is 2, 3 or 4.

9. The heptapeptide analogue according to claim 8 selected from:

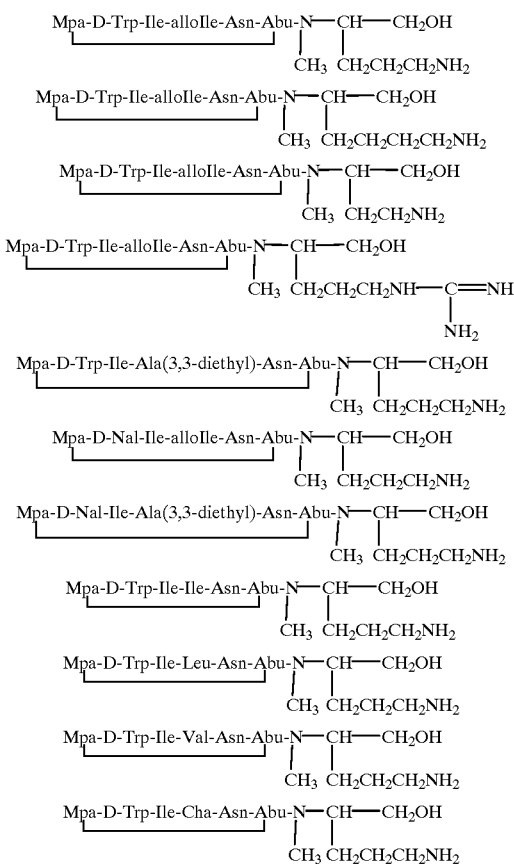

10. The heptapeptide analogue of claim 1 having the structure:

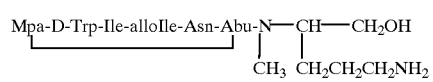

11. The heptapeptide analogue of claim 1 having the structure:

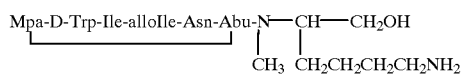

12. The heptapeptide analogue of claim 1 having the structure:

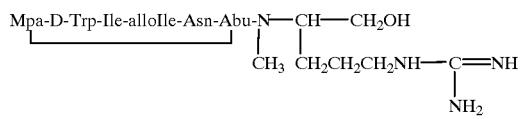

13. The heptapeptide analogue of claim 1 having the structure:

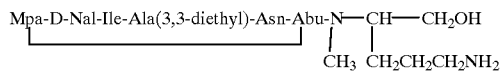

14. The heptapeptide analogue of claim 1 having the structure:

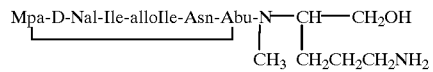

15. A pharmaceutical composition comprising a pharmacologically effective amount of a heptapeptide analogue of claim 1 and a pharmaceutically acceptable carrier.

16. The composition of claim 15 which is an aqueous solution for nasal, subcutaneous or intravenous administration.

17. The composition of claim 15, wherein the carrier includes a buffering agent.

18. The composition of claim 15, in the form of a tablet, a capsule, granules, and similar, for oral administration.

19. A method of treatment of pre-term labour which is the administration to a woman in need of such treatment of a composition of claim 15.

20. A method for preparing a heptapeptide analogue, or a pharmaceutically acceptable salt thereof, having oxytocin antagonist activity and consisting of a hexapeptide moiety S and a C-terminal β-aminoalcohol residue Z bound to the moiety S by an amide bond, wherein the β-aminoalcohol Z is:

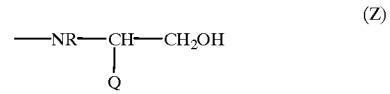

wherein Q is $(CH_2)_n$—NH—A, n is 1–6 and A is H or —C(=NH)NH$_2$ and wherein R is CH$_3$ or C$_2$H$_5$; and the moiety S is:

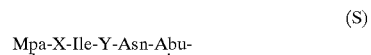

wherein Mpa, Ile, Asn and Abu have the following meaning

| Mpa | 3-mercaptopropionic acid residue |
| --- | --- |
| Ile | isoleucine residue |
| Asn | asparagine residue |
| Abu | α-aminobutyric acid residue; | and wherein X is a D-aromatic α-amino acid; and Y is an aliphatic α-amino acid, by reducing a corresponding compound wherein Z is Y:

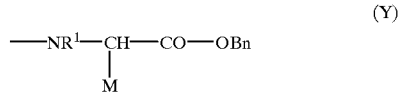
(Y)

wherein M is $(CH_2)_n$—N(Pht) or —$(CH_2)_n$—N(P)—C(=NP)NP$_2$ wherein one or two of the groups P are nitrogen protecting groups and the rest are hydrogen, n is 1–6, and R$^1$ is CH$_3$ or C$_2$H$_5$,
using a borohydride salt or a substituted borohydride or borane.

21. The method of claim 20, wherein the borohydride is NaBH$_4$.

22. The method of claim 21, wherein the composition is an intimate mixture of the heptapeptide analogue or salt thereof and the carrier.

23. The method of claim 22, comprising covering said mixture with an enteric coat, in particular an enteric coat not readily soluble at pH 5.0 and lower.

24. The method of claim 22 or 23, comprising tabletting or granulating the mixture and/or filling it into a capsule.

25. A method for reducing or blocking the contraction of uterine muscle, comprising administering to a woman in need of treatment therefor an effective amount of a heptapeptide analog as defined in claim 1.

26. A method for reducing or blocking the contraction of uterine muscle, comprising administering to a woman in need of treatment therefor an effective amount of a heptapeptide analog as defined in claim 15.

27. The method of claim 26, wherein the uterine muscle contraction is associated with pre-term labor.

28. The method of claim 26, wherein the uterine muscle contraction is associated with menstrual pain.

* * * * *